United States Patent [19]

Geluk et al.

[11] Patent Number: 5,044,007

[45] Date of Patent: Aug. 27, 1991

[54] IMPROVED SLIT RADIOGRAPHY ASSEMBLY HAVING AN X-RAY SOURCE OF VARIABLE HARDNESS SYNCHRONIZED TO VARYING SLIT HEIGHT

[75] Inventors: Ronald J. Geluk, Nootdorp; Hugo Vlasbloem, Maasland, both of Netherlands

[73] Assignee: B.V. Optische Industrie "De Oude Delft", Delft, Netherlands

[21] Appl. No.: 458,706

[22] PCT Filed: Jul. 26, 1988

[86] PCT No.: PCT/EP88/00676

§ 371 Date: Jan. 30, 1990

§ 102(e) Date: Jan. 30, 1990

[87] PCT Pub. No.: WO89/01280

PCT Pub. Date: Feb. 9, 1989

[30] Foreign Application Priority Data

Aug. 3, 1987 [NL] Netherlands .......................... 8701820

[51] Int. Cl.[5] .......................... G21K 5/10; G21K 3/00; G21K 1/04

[52] U.S. Cl. .................................... 378/146; 378/113; 378/156; 378/160

[58] Field of Search ................ 378/145, 146, 151, 152, 378/153, 109, 110, 111, 112, 113, 156-160

[56] References Cited

U.S. PATENT DOCUMENTS

| 4,675,893 | 6/1987 | Duinker et al. ..................... 378/151 |
| 4,677,652 | 6/1987 | Duinker et al. ..................... 378/146 |
| 4,715,056 | 12/1987 | Vlasbloem et al. ................. 378/152 |
| 4,785,471 | 11/1988 | Boersma ............................. 378/146 |

FOREIGN PATENT DOCUMENTS

| 0059382 | 9/1982 | European Pat. Off. . |
| 0158382 | 10/1985 | European Pat. Off. . |
| 0188783 | 7/1986 | European Pat. Off. . |
| 0209930 | 1/1987 | European Pat. Off. . |
| 0220770 | 5/1987 | European Pat. Off. . |
| 3141041 | 4/1983 | Fed. Rep. of Germany . |

Primary Examiner—Edward P. Westin
Assistant Examiner—Kim-Kwok Chu
Attorney, Agent, or Firm—Louis E. Marn

[57] ABSTRACT

An apparatus for slit radiography is provided with a slot diaphragm to form a fan-shaped X-ray beam with which a body can be scanned. Controllable attenuating elements interact with the slit diaphragm to influence sectors of the fan-shaped X-ray beam. They are controlled by signals representing the instantaneous transmission of the body in the corresponding sectors. The hardness of the fan-shaped X-ray beam is varied periodically in a predetermined manner. Synchronously with the periodic variation of the hardness of the X-ray beam the attenuating elements are oscillated. The oscillation of the attenuating elements is superimposed at each instant on the instantaneous position determined by the signals representing the instantaneous body transmission. The amplitude of the oscillation is less than the height of the slit of the slit diaphragm. The influence on the X-ray beam is most at the instants at which the hardness is greatest.

13 Claims, 1 Drawing Sheet

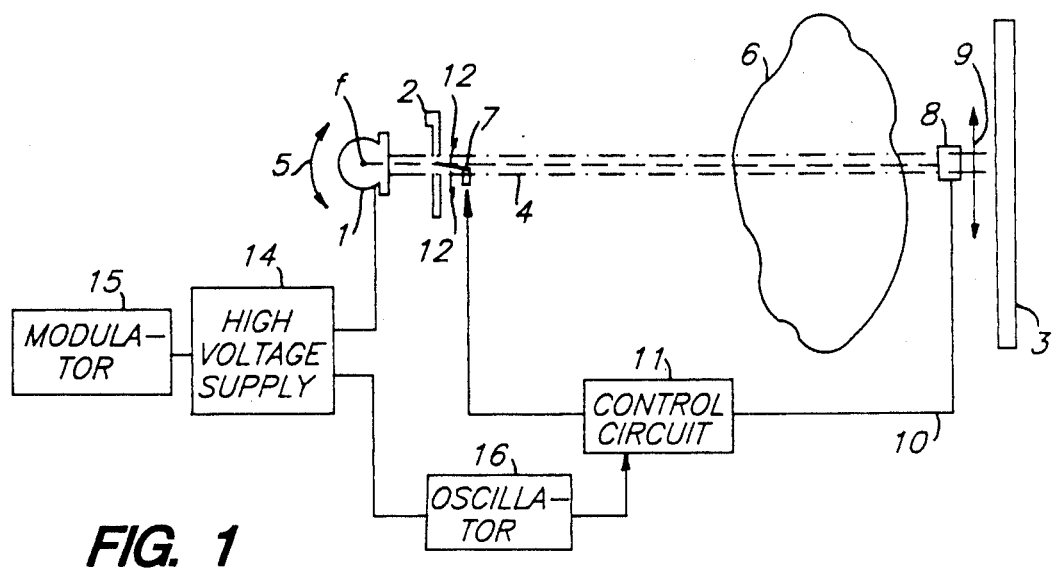
FIG. 1
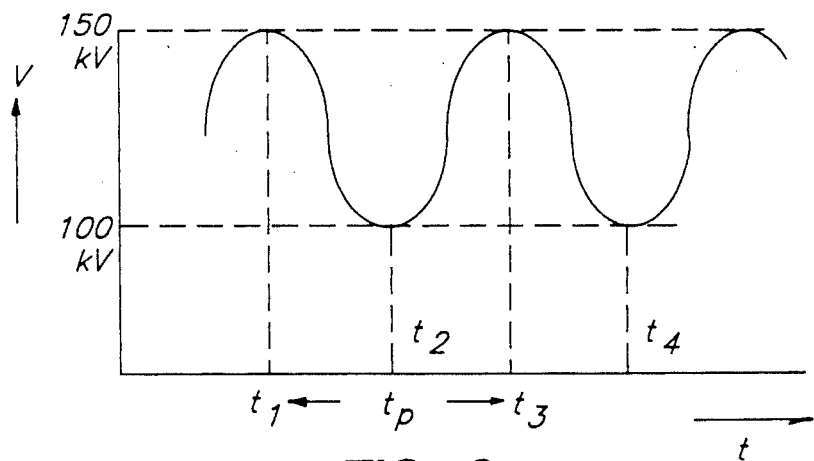
FIG. 2
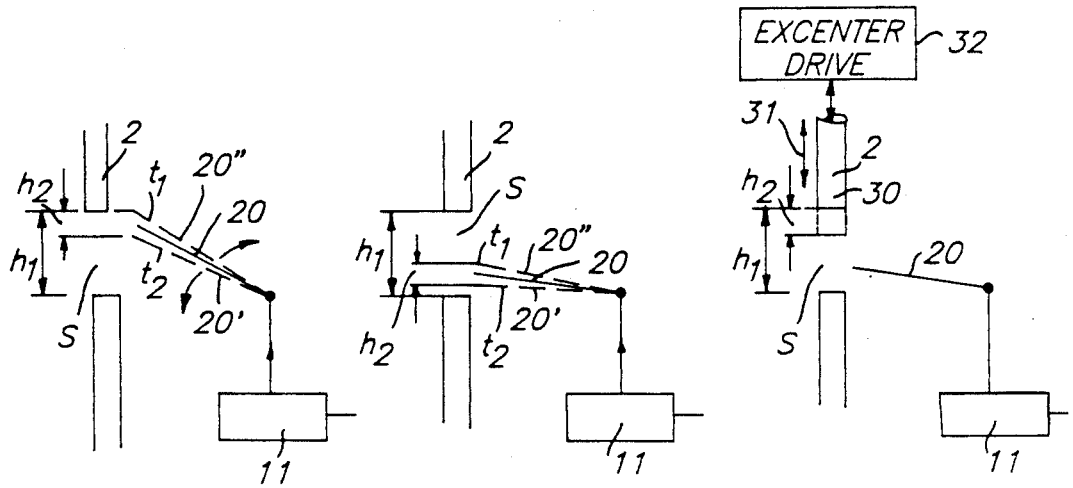
FIG. 3   FIG. 4   FIG. 5

IMPROVED SLIT RADIOGRAPHY ASSEMBLY HAVING AN X-RAY SOURCE OF VARIABLE HARDNESS SYNCHRONIZED TO VARYING SLIT HEIGHT

BACKGROUND OF THE INVENTION

(1) Field of the Invention

The invention relates to a device for slit radiography comprising an X-ray source; a slit-shaped diaphragm which is placed in front of the X-ray source and forms a fan-shaped X-ray beam during operation with which a body to be examined can at least partially be scanned for the formation of an X-ray shadow image of the scanned part of the body on an X-ray detector placed behind the body; a control signal generator which feeds a signal representing the instantaneous transmission of the body to control means during operation per sector of the fan-shaped X-ray beam; controllable attenuating elements which interact with the slit diaphragm and can influence the fan-shaped X-ray beam per sector under the control of control signals provided by the control means.

(2) Description of the Invention

A device cf this type is known from Dutch Patent Application 8,400,845. According to the technique known from Dutch Patent Application 8,400,845, the quantity of X-rays transmitted at any time by the slit diaphragm is regulated by using attenuating elements which are placed at or in the slit of the slit diaphragm, can each influence one sector of the fan-shaped X-ray beam and are controlled depending on the attenuation occurring in the associated sector and caused by the body to be examined, in a manner such that the attenuating elements reach into the X-ray beam to a greater or lesser extent. If the attenuation caused by the irradiated body in a specific sector at a specific instant is high the attenuating element belonging to this sector is moved entirely or considerably out of the X-ray beam. If, on the other hand, the attenuation caused by the body in a specific sector at a specific instant is low the associated attenuating element is brought further into the X-ray beam.

It is an advantage of this technique that equalized radiographs, that is radiographs having been exposed correctly both in the light parts and in the dark parts, can be obtained therewith. Accordingly, if, for example, an image is taken in this manner of the upper part of a patient's body the radiologist can find sufficient information, in one and the same image, about both the lungs and the abdomen of the patient whereas two different images have so far been necessary to obtain the same information.

The known technique has the drawback that in principle X-rays of the same hardness are used for both the transparent parts and for opaque parts of the patient, whereas a relatively greater X-ray hardness is desired for the opaque parts than for the transparent parts in order to obtain better exposure in the opaque parts and better contrast of the X-ray shadow image to be formed in the transparent parts.

The invention therefore aims at improving the known technique and generally at providing an effective device for making equalized radiographs.

SUMMARY OF THE INVENTION

For this purpose, a device of the type described is characterized according to the invention by means for periodically varying, in a predetermined manner, the hardness of the fan-shaped X-ray beam and by means for simultaneously oscillating all the attenuating elements, the oscillation being superimposed at each instant on the instantaneous position, determined by the control signals, of each attenuating element, having a predetermined amplitude which is less than the height of the slit of the slit diaphragm and being synchronous with the periodic variation in hardness, such that each attenuating element influences the X-ray beam most at the instants at which the hardness is greatest.

BRIEF DESCRIPTION OF THE INVENTION

In the text which follows, the invention will be described in detail with reference to the accompanying drawing, in which FIG. 1 shows diagrammatically an example of a device for slit radiography, the invention being applied;

FIG. 2 shows a periodically varying supply voltage for an X-ray tube; and

FIGS. 3 and 4 illustrate diagrammatically a cross-section through a slit diaphragm having a single attenuating element in various positions.

FIG. 5 shows a variant of FIG. 3 and FIG. 4.

DETAILED DESCRIPTION OF THE INVENTION

FIG. 1 diagrammatically shows an example of a device for slit radiography comprising an X-ray source 1, a slit diaphragm 2 placed in front of the X-ray source and an X-ray screen 3. The slit diaphragm 2 transmits a fan-shaped X-ray beam 4 with a relatively small thickness. During operation, the X-ray source and/or the slit diaphragm are moved such that the X-ray beam 4 scans the X-ray detector 3. For this purpose, for example, the X-ray source can be pivoted together with the slit diaphragm about an axis extending transverse to the plane of projection through the X-ray focus f, as indicated by an arrow 5. When a body 6 to be irradiated is present between the X-ray source and the X-ray detector, a radiograph can be taken of (a part of) the body 6 in this manner. It is to be noted that a strip-shaped X-ray detector can also be used instead of a stationary X-ray detector in the manner described in Dutch Patent Application 8,303,156.

In order to be able to influence the quantity of X-rays transmitted by the slit diaphragm per sector of the fan-shaped X-ray beam for making an equalized radiograph, controllable attenuating elements 7 interacting with the slit diaphragm are present. The attenuating elements can be designed in various ways as described, for example, in Dutch Patent Application 8,400,845. In the example shown in FIG. 1, the attenuating elements are tongue-shaped and the free ends of the tongues can be pivoted to a greater or lesser extent into the X-ray beam under the influence of appropriate control signals, as shown by arrows 12. The attenuating elements can, however, for example also be plate-shaped as is also described in Dutch Patent Application 8,400,845.

For generating the control signals required for the attenuating elements a detector is present which is located behind the body 6 to be irradiated, detects the radiation transmitted via the body 6 per sector of the X-ray beam and generates corresponding electrical signals. The detector may consist of a row of light detectors which are located behind the X-ray screen at the height of the incident beam and which detect the quantity of light generated by the X-ray screen 3 under the influence of the incident X-rays. It is also possible to detect the X-rays transmitted by the X-ray screen 3. The detector may also be located in front of the X-ray screen and then consist, for example, of an elongate dosimeter as described, for example, in Dutch Patent Applications 8,503,152 and 8,503,153 by the Applicant.

A dosimeter of this type is diagrammatically shown at 8 in FIG. 1 and is moved along synchronously with the scanning X-ray beam as indicated by an arrow 9. The signals derived from the dosimeter are fed via an electrical line 10 to a control circuit 11 which forms the control signals for the attenuating elements.

The starting point in the previously described technique is a constant spectrum of the X-ray beam emitted by the X-ray source before this is influenced by the attenuating elements.

By contrast, according to the invention the hardness of the X-ray beam is varied in a predetermined fixed manner while a sector-wise influencing of the X-ray beam also takes place with the aid of the attenuating elements. As will be evident in the text which follows, a fixed oscillation is moreover superimposed on the variable movements, caused by the control signals, of the attenuating elements synchronous with the variation in hardness.

The predetermined fixed influencing of the X-ray beam can be brought about by modulating the high supply voltage of the X-ray tube with a fixed ripple voltage. On use of a ripple voltage having standard frequency (50 Hz or 60 Hz) the high voltage supply, diagrammatically shown at 14 in FIG. 1, for the X-ray tube may be relatively inexpensive because no measures are then necessary for eliminating the ripple which is always present in the supply voltage and are caused by the standard frequency. A separate modulator is diagrammatically shown at 15.

FIG. 2 shows an example of a modulated supply voltage V for the X-ray tube. Such a voltage can be obtained in a simple manner by unilateral rectification and flattening of a normal sinusoidal alternating voltage. The value of the supply voltage of the X-ray tube determines the hardness of the X-rays in particular such that the hardness of the X-rays increases with a higher V value. Therefore, an X-ray tube energized with a supply voltage of the form shown emits an X-ray beam the hardness of which increases synchronously with the supply voltage periodically from a minimum value to a maximum value and subsequently decreases again to the minimum value.

In the example of FIG. 2, the supply voltage of the X-ray tube varies between 150 kV and 100 kV with a period tp which can, for example, be 20 msec corresponding to a modulation frequency of 50 Hz.

Another modulation depth and/or another level of the supply voltage and/or another modulation frequency can of course be used.

FIG. 3 diagrammatically shows a cross-section of a slit diaphragm and a single attenuating element in a position belonging to a relatively transparent irradiated part of a body to be examined. FIG. 4 shows a similar view in which the position of the attenuating element corresponds to an opaque part of the body.

The slit diaphragm is indicated at 2 in FIGS. 3 and 4 and the slit S has a height $h_1$. Furthermore, a tongue-shaped attenuating element 20 the position of which relative to the slit S is determined at each instant by control signals of the control circuit 11 is shown in the two figures.

The slit S has a certain length in the direction transverse to the plane of projection, and a number of attenuating elements is placed next to each other in this direction so that each attenuating element can influence a specific sector of the fan-shaped X-ray beam transmitted by the slit.

The attenuating element 20 shown in FIG. 3 is in a position such that the slit S is closed locally over virtually the entire length $h_1$. This means that the body to be examined is very transparent in the corresponding sector of the fan-shaped X-ray beam. For correct exposure of the X-ray detector 3 it is therefore necessary to intercept a large part of the available X-rays in this sector at the instant of scanning. This is effected by bringing the attenuating element into the position shown in FIG. 3. This manner of controlling attenuating elements is already known from Dutch Patent Application 8,400,845 from which it is also known that the attenuating elements may also have a different shape.

According to the invention, the attenuating elements, in addition to being set in motion by the control signals described which are proportionate to the local transparency of the body, are furthermore set into motion by an additional control signal causing an oscillation with a fixed amplitude. The peak-peak value of the oscillation is given as $h_2$ in FIGS. 3 and 4. In a device in practice, $h_2$ may be, for example, 10 to 20% of $h_1$. The extreme positions of the attenuating elements 20 relative to the position proportional to the local transparency are indicated by broken lines at 20' and 20" in FIGS. 3 and 4.

The oscillation between positions 20' and 20" takes place, according to the invention, synchronously with the variation in the hardness of the X-rays and thus synchronously with the amplitude modulation, shown in FIG. 2, of the supply voltage of the X-ray tube. This oscillation takes place such that the attenuating elements are in each case in position 20" and thus influence the X-ray beam most, at times $t_1$, $t_3$, etc. at which the supply voltage of the X-ray tube has the highest value. The attenuating elements are also in each case in position 20' at times $t_2$, $t_4$, etc., at which the supply voltage of the X-ray tube has the lowest value.

All this has the following result. During scanning of relatively transparent parts of a body to be examined the attenuating elements 20 are brought into a position, by the control circuit 11, in which the X-rays are largely stopped. Such a position of an attenuating element in which an attenuating element covers the slit S over virtually the entire height is shown in FIG. 3. Moreover, at times $t_1$, $t_3$, etc. at which the offered X-rays have the greatest hardness the slit is covered still further as a result of the oscillation of the attenuating elements. The hard radiation is therefore very considerably stopped. At the instants $t_2$, $t_4$, etc. at which the offered X-rays have the lowest hardness the attenuating elements leave the slit S exposed over a relatively large section (position 20' in FIG. 3). Transparent parts of the body to be examined are therefore irradiated with relatively soft X-rays and a good contrast in the final image is obtained.

During scanning of relatively little transparent parts of the body to be examined the attenuating elements are brought by the control circuit 11 into a position such that only a very small section of the height of the slit S is covered. All this is shown in FIG. 4. Although the slit S is also covered over a greater height in this situation at the instants at which the offered X-rays have the greatest hardness the slit nevertheless remains substantially exposed and the oscillation of the attenuating elements has relatively little influence. The parts of the body to be examined which are of low transparency are therefore exposed to relatively high energetic radiation.

The desired periodic oscillation of the attenuating elements can be brought about in a simple manner by superimposing a periodic signal on the control signals provided by the control circuit 11. A separate oscillator 16 can be used for this purpose as shown, but such an oscillator may also be incorporated in the control circuit. As already mentioned, the oscillation ought to be synchronous with the variation in the supply voltage of the X-ray tube. To this end, the device 16 may be coupled to the supply circuit 14 of the X-ray tube, as shown in FIG. 1, or to the modulator 15.

Oscillation of the attenuating elements may, however, also be brought about in a different manner, for example, by means of direct control of the attenuating elements by the device 16 or by causing a common support of the attenuating elements to oscillate.

Following the above, divers modifications are obvious to a person of ordinary skill in the art.

Thus for example the amplitude of the common oscillation of an attenuating element can be related to the degree in which such element covers the slit S. For example the amplitude of the oscillation could be greater in proportion as an attenuating element more covers the slit. Such a 'position dependent' amplitude of oscillation for example can be achieved by adding the signals originating from the detector 8 to the signals bringing about the common oscillation and by amplifying the sumsignal thus obtained until a control signal component of the desired value has been obtained. The amplitude of the periodic signal bringing about the oscillation then automatically is also amplified to a degree dependent on the necessary control signal.

Furthermore it is possible to make not the attenuating elements but the upper edge of the slit S or the whole slit oscillate periodically in synchronism with the periodic variation in hardness. 'Upper edge of the slit S' in this context means that edge of the slit which is farthest away from the position of rest of the attenuating elements.

One thing and another is shown in FIG. 5. FIG. 5 mainly corresponds with FIGS. 3 and 4 but now the attenuating elements are controlled in the usual way while the slit diaphragm 2 or at least its upper edge 30 are being oscillated in the plane of the slit S as shown by double arrow 31. For that purpose use can for example be made of an excenter-drive 32. Furthermore appropriate guides have to be present for the oscillating (part of the slit diaphragm.

The peak-peak value of the oscillation again has been indicated by $h_2$.

Those and similar modifications are considered to fall within the scope of the invention.

We claim:

1. A slit radiography assembly, which comprises:
an X-ray source
means for periodically varying the hardness of a fan-shaped X-ray beam during scanning;
a slit diaphragm positioned between said X-ray source and a body being radiographed for forming a fan-shaped X-ray beam;
means for scanning said body with said fan-shaped X-ray beam;
a plurality of attenuating elements disposed along said slit diaphragm for influencing said fan-shaped X-ray beam during scanning;
detection means for detecting the quantity of X-ray radiation transmitted through said body during scanning and converting said detected quantity into corresponding signals;
control means for receiving said corresponding signals and for forming control signals corresponding to said signals from said detected quantity of transmitted X-ray radiation;
means for transmitting said control signals to said attenuating elements; and
means for simultaneously oscillating said attenuating elements on a predetermined amplitude less than a height of said slit diaphragm, oscillation of said attenuating elements being synchronized with periodic variation of greater hardness of said fan-shaped X-ray beam to more greatly influence said hardness of said fan-shaped X-ray beam.

2. A slit radiography assembly which comprises:
an X-ray source;
means for periodically varying the hardness of an X-ray beam;
a slit diaphragm positioned between said X-ray source and a body being radiographed for forming a fan-shaped X-ray beam;
means for scanning said body with said fan-shaped beam;
means for oscillating during scanning an edge of said slit diaphragm in a predetermined amplitude less than a height of said slit diaphragm, oscillation of said edge of said slit diaphragm being synchronized to more greatly influence said hardness of said fan-shaped X-ray beam with the periodic variations of greater harness of said fan-shaped X-ray beam;
detection means for detecting the quantity of X-ray radiation transmitted through said body during scanning and converting said detected quantity into corresponding signals;
control means for receiving said signals and for forming control signals corresponding to said signals from said detected quantity of transmitted X-ray radiation; and
means for transmitting said control signals to said attenuation elements.

3. The slit radiography assembly as defined in claim 1 or 2 wherein said means for periodically varying hardness of said fan-shaped X-ray beam modulates a supply voltage of said X-ray source.

4. The slit radiography assembly as defined in claim 3 wherein a modulator is connected to said supply voltage of said X-ray source.

5. The slit radiography assembly as defined in claim 2 wherein said means for oscillating said edge of said slit diaphragm is an excenter-drive.

6. The slit radiography assembly as defined in claim 1 wherein said means for simultaneously oscillating said attenuating elements is an oscillator.

7. The slit radiography assembly as defined in claim 6 wherein said oscillator directly controls the attenuating elements.

8. The slit radiography assembly as defined in claim 6 wherein said oscillator provides an electrical signal to said control means.

9. The slit radiography assembly as defined in claim 8 wherein said oscillator is incorporated in said control means.

10. The slit radiography assembly as defined in claim 1 wherein said means is simultaneously oscillating said attenuating elements is a common support of said attenuating elements.

11. The slit radiography assembly as defined in claim 2 wherein said means for oscillating said edge of said slit diaphragm is an excenter-drive.

12. The slit radiography assembly as defined in claim 1 wherein said means for simultaneously oscillating said attenuating elements adjusts the amplitude of oscillation of an attenuating element in dependence upon the degree in which said attenuating element influences said X-ray beam.

13. The slit radiography assembly as defined in claim 12 wherein said amplitude of oscillation of an attenuating element is adjusted to a value greater in proportion as said attenuating element influences said X-ray beam greater.

* * * * *